United States Patent [19]

Flower

[11] Patent Number: 5,688,232
[45] Date of Patent: Nov. 18, 1997

[54] IONTOPHORETIC DRUG DELIVERY DEVICE HAVING AN IMPROVED CONTROLLER

[75] Inventor: Ronald J. Flower, Vernon, N.J.

[73] Assignee: Becton Dickinson and Company, Franklin Lakes, N.J.

[21] Appl. No.: 535,447

[22] Filed: Sep. 28, 1995

[51] Int. Cl.$^6$ .................................................. A61N 1/30
[52] U.S. Cl. ................................................................. 604/20
[58] Field of Search ................. 604/19–20; 607/1–3, 607/59, 62–63

[56] References Cited

U.S. PATENT DOCUMENTS

| | | | |
|---|---|---|---|
| 4,822,334 | 4/1989 | Tapper | 607/63 |
| 5,224,928 | 7/1993 | Sibalis et al. | 604/20 |
| 5,246,418 | 9/1993 | Haynes et al. | 604/20 |
| 5,256,137 | 10/1993 | Sage, Jr. | 604/20 |
| 5,306,235 | 4/1994 | Haynes | 604/20 |

*Primary Examiner*—Mark Bockelman
*Assistant Examiner*—Ellen S. Tao
*Attorney, Agent, or Firm*—Allen W. Wark

[57] ABSTRACT

An iontophoretic system includes a medicament containing disposable patch removably attached to a patient's skin in combination with a controller mechanism. The patch includes an anode and a cathode, and holds an electrolyte and a medicament. The controller includes a controller circuit which is coupled to the cathode and is adjustable to provide a desired current flow through the electrodes to drive the medicament to the skin of the patient. The controller preferably includes a variety of functions to ensure safe and proper delivery of the medicament. The controller circuit is preferably an application specific integrated circuit (ASIC) so as to provide a compact controller having increased reliability and reduced power consumption.

21 Claims, 3 Drawing Sheets

IONTOPHORETIC DRUG DELIVERY DEVICE HAVING AN IMPROVED CONTROLLER

BACKGROUND OF THE INVENTION

1. Field of the Invention

The present invention relates to an improved iontophoretic drug delivery system, and more specifically relates to a controller and drug delivery patch having features which improve the transdermal delivery of a drug or medicine.

2 Description of the Prior Art

Iontophoresis may be defined as the non-invasive transdermal delivery of a substance. This process has become an increasingly popular and effective method for the delivery of pharmaceuticals. Such systems offer advantages which are clearly not achievable by other drug administration methods such as injection and ingestion.

Presently, known iontophoretic devices use at least two electrodes, which are in contact with a portion of a patient's body. A first electrode, typically called the active electrode, delivers an ionic substance (medicament) into the body by iontophoresis. The second electrode, typically called the counter electrode, closes an electrical circuit that includes the first electrode, the patient's body and an energy source such as a battery. The medicament to be driven into the body by the first electrode may be either positively charged or negatively charged. In the case of a positively charged medicament, the anode of the iontophoretic device becomes the active electrode and the cathode serves as the counter electrode. Alternatively, if the medicament is negatively charged, the cathode will be the active electrode and the anode will be the counter electrode.

One type of iontophoretic drug delivery device includes a separate, reusable controller, which can be removably, electrically coupled to a disposable patch that remains attached to the user. The controller includes the electronics that regulate the amount and duration of drug delivery. Iontophoretic delivery of a substance to a patient may be accomplished in a variety of ways such as at a relatively fast constant rate or at a relatively slow periodic rate. Therefore, it may be necessary for the drug-containing patch to be maintained in contact with the patient's skin for extended time periods.

In situations where the periodic delivery of the medicament is preferred, there is no need to maintain electrical contact between the controller and the patch between drug deliveries. While the unobtrusive drug-containing patch may remain attached to the patient, detachment of the controller permits the patient to be free from the cumbersome connection to the energy source. When iontophoretic drug delivery is once again desired, the controller can be reconnected to the patch. Since the energy source generally includes a depletable battery, it would be helpful if the controller electronics included means for recording the number of times the controller is used, the duration of each use, the charge remaining in the battery as well as the time elapsed since manufacture. In this manner, one can better ensure that the controller's energy source has sufficient charge and the controller electronics are still useful to properly transdermally deliver the medicament to the patient.

It is known that certain medicaments are most effective when provided for a specific duration at specific periodic intervals and at specific rates of delivery. Therefore, it would also be helpful to provide a controller that is able to deliver medicaments not only at constant rates or periodic intervals, but can regulate the rate of delivery. Additionally, it is known that a user may experience discomfort and adverse effects when exposed to a rapid change in current and/or voltage, and a quantity of coulombs in excess of a specified amount. Therefore, it would be helpful to provide iontophoretic delivery wherein the rate of delivery is regulated in accordance with the characteristics of the drug being delivered, a change in rate of current and/or voltage is limited, and wherein the total quantity of coulombs provided is monitored.

As previously noted, it may be necessary to use an iontophoretic drug delivery device over an extended period of time. As the length of delivery time increases, there is a need to develop a controller which is unobtrusive to the user. In addition, as medical personnel discover that a wide variety of medicaments may be iontophoretically delivered, it would be helpful to provide a controller that can be programmed to deliver a variety of drugs. It would also be helpful if the controller could identify the type of drug being delivered, deliver the drug according to a specific delivery profile, and prevent any controller from delivering current to the patch once the medicament has been delivered to the patient.

The electronic circuits contained in the controller in known drug delivery devices typically utilize discrete electronic components. The circuits provided by the combination of these discrete electronic components are relatively large in size. Therefore, in order to provide an unobtrusive controller, a multitude of functions are typically not incorporated in known iontophoretic devices. In addition, in transdermal delivery devices where discrete electronic components are utilized, the reliability of the controller is relatively low because each of the discrete components has different performance characteristics and rates of failure. Therefore, it would be helpful to design a controller that is small enough to be unobtrusive to the user, yet includes a number of features to improve delivery of the medicament, wherein the reliability of the controller is increased.

OBJECTS AND SUMMARY OF THE INVENTION

It is an object of the present invention to provide an iontophoretic drug delivery system having a controller including an electronic control circuit that permits the reliable delivery of a medicament.

It is a further object of the present invention to provide an iontophoretic drug delivery system having a controller including an electronic control circuit that is smaller in size than traditional iontophoretic electronic control circuits performing at least substantially the same functions.

It is another object of the present invention to provide an iontophoretic drug delivery system including a medicament containing patch and a controller having safety features to ensure the proper delivery of a medicament to a user.

It is still another object of the present invention to provide an iontophoretic drug delivery system including a medicament containing patch and a controller having user interface features to ensure the proper delivery of the medicament to a user.

It is yet another object of the present invention to provide an iontophoretic drug delivery system having a controller including an electronic control circuit that has a lower power consumption and is more reliable than traditional iontophoretic electronic control circuits performing substantially the same functions.

It is still a further object of the present invention to provide an iontophoretic drug delivery system having a controller that includes an electronic control circuit which overcomes the inherent disadvantages of known iontophoretic drug delivery devices.

In accordance with one embodiment of the present invention, the iontophoretic drug delivery device includes a medicament-containing disposable patch having first and second electrodes and a reusable controller selectively connectable to the patch. The patch is removably attachable to the skin of the patient for transdermal delivery of an ionized medicament. The controller includes an energy source that powers the patch to drive the ionized medicament transcutaneously to the patient. The controller also includes a controller circuit, a microprocessor and an E²PROM. The controller circuit includes an adjustable current regulator circuit having a current control circuit, a duration timer circuit, a delivery profile circuit and a rate of current change limiter circuit for generating a desired current flow through the first and second electrodes of the patch to control the delivery of the medicament. The controller circuit also includes a means for sensing a number of times the controller is used. In this manner, the useful life of the iontophoretic controller can be tracked. In order to accomplish this task, the iontophoretic drug delivery device includes a treatment counter circuit which counts the number of times the controller is activated. The treatment counter circuit may send a control signal to the microprocessor rendering the controller unusable when a specific number of activations have been sensed. The controller may further include a display for displaying the number of times the controller has been used and for indicating whether a useful life of the controller has expired.

In an alternative embodiment, the iontophoretic drug delivery device includes a life timer circuit having a clock, which can be started at the date of manufacture, for timing a useful life of the controller. For example, the power source and controller electronics may have a life expectancy of approximately 5 years. Accordingly, when the clock has timed 5 years from the date of manufacture, the controller is no longer usable and should be discarded. The controller circuit may include means to indicate that the useful life has expired. When the life timer circuit determines that the usable life of the controller has expired, the life timer circuit sends a control signal to the microprocessor which will render the controller unusable.

The iontophoretic drug delivery system of the present invention also includes an E²PROM, having sufficient memory, coupled to the microprocessor for recording a date, time and/or duration of usage by the patient. This stored information can be retrieved by a health-care professional to evaluate patient compliance in receiving medication as prescribed. In order to retrieve the recorded information, the controller includes a means of communication which can be serial and can be transmitted by optical, electromagnetic, or direct electrical contact methods.

As a further means to monitor the energy remaining in the energy source, the controller circuit includes a battery monitor coupled to the energy source which checks the amount of charge remaining. The battery monitor circuit provides a control signal to the microprocessor instructing the microprocessor to disable the controller when the voltage in the energy source falls below a predetermined value. The controller circuit may also include a coulombmeter for measuring the total number of electrons provided from the controller to the patch. The controller circuit may further include a patch identification (ID) detector coupled to a patch ID indicator of the patch for determining whether the patch and controller are compatible, a current monitor circuit monitoring the amount of current flow from the current regulator circuit through the patch, a voltage monitor circuit monitoring the voltage potential between the first and second electrodes, and a patch marker circuit which activates a fuse in the patch once the medicament on the patch has been substantially utilized.

The controller may also include a voltage converter coupled to the energy source which generates an output voltage that is provided to at least one of the first and second electrodes. The voltage converter is responsive to a voltage drop across the first and second electrodes. The voltage converter adjusts its output voltage in response to the voltage drop to provide just the voltage needed across the electrodes for safe and effective drug delivery to the patient without the wasteful consumption of power.

The iontophoretic device in accordance with the present invention may also include a unique serial number stored in the read only memory (ROM) of the microprocessor. The purpose of the unique serial number is for traceability or tracking of the controller. Accordingly, the controller can be tracked to determine which patient has a particular controller. Furthermore, the unique controller serial number may be used as a security device preventing the inappropriate use of the controller by the patient or others.

In accordance with another form of the present invention, the controller circuit of the iontophoresis system is an application specific integrated circuit (ASIC). The ASIC includes the integration of substantially all of the active electronic components of an iontophoretic drug delivery control circuit and substantially all of the controller features.

The ASIC is designed to include functions performed by individual circuits in traditional controllers. Specifically, the ASIC includes incorporation of a current control and delivery mechanism, a current delivery safety mechanism, a system control mechanism and a user interface mechanism. The current control and delivery mechanism includes a current control circuit, a voltage converter, a current delivery duration timer circuit, a current delivery profile circuit, and a rate of change in current limiter circuit. The current control and delivery circuit may also include a microprocessor. The current delivery safety mechanism includes a coulombmeter, a voltage monitor circuit, current monitor circuit, a patch identification circuit and a patch marker circuit. The user interface mechanism includes light emitting diode (LED) drivers, device life timer circuit, treatment counter circuit, battery monitor circuit, and a data storage circuit.

A preferred form of the iontophoretic drug delivery system including a controller and an iontophoretic patch as well as other embodiments, objects, features and advantages of this invention, will be apparent from the following detailed description thereof, which is to be read in connection with the accompanying drawings.

DETAILED DESCRIPTION OF THE PREFERRED EMBODIMENTS

Figure 1:
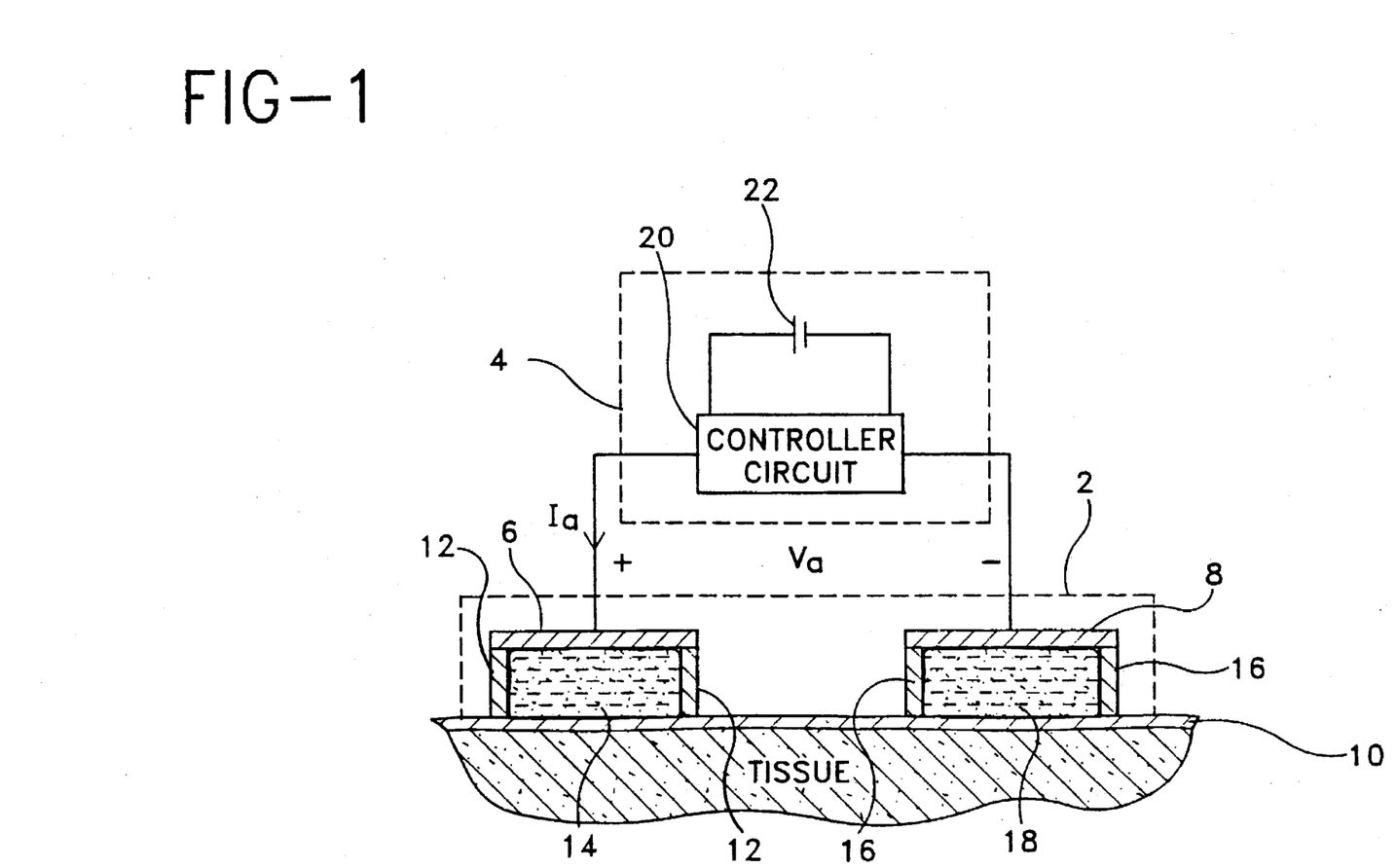
FIG. 1 is a functional block diagram of the iontophoretic drug delivery system formed in accordance with the present invention, with portions thereof shown in cross-section.

Referring initially to FIG. 1 of the drawings, it will be seen that an iontophoretic system for delivering medication to a patient transdermally, that is, through the skin of the patient, basically includes a transdermal drug delivery device, commonly referred to as a patch 2, for placement against the epidermis 10 of a patient, and a controller 4 which is electrically coupled to the patch 2, for controlling the drug delivery.

One form of a transdermal drug delivery device is illustrated by FIG. 1. The patch 2 basically includes a first electrode 6, which may act as an anode, and a second electrode 8, which may act as a cathode. The patch is detachably placeable against the epidermis 10 of a patient so that the anode electrode 6 and cathode electrode 8 are in electrical communication with the patient.

Adjacent to the first electrode 6 is a container 12 or other suitable structure defining a well for holding a medicament 14 in place between the first electrode 6 and the epidermis 10. Similarly, adjacent to the second electrode 8 is a container 16 or other suitable structure forming a well for holding an electrolyte 18 in place between the second electrode and the epidermis 10. Alternatively, the container 16 holds the medicament 14 while the container 12 holds the electrolyte 18.

When a voltage Va is impressed across the first and second electrodes 6, 8, current Ia will flow through the epidermis 10, driving the medicament 14, which may be ionic or non-ionic, into the patient's skin and tissue for absorption therein. To simplify the explanation, only two electrodes are shown in FIG. 1. However, it should be understood that each anode and cathode may be segmented, or multiple electrodes may be provided, as is known in the art.

Referring again to FIG. 1 of the drawings, the controller 4 of the iontophoretic drug delivery device includes a controller circuit 20 capable of providing a plurality of iontophoretic drug delivery functions. The controller 4 may also include a power source 22, such as a battery, which is electrically coupled to the controller circuit 20. The controller circuit 20 is coupled to the transdermal patch 2 to provide a controlled current through, and voltage across, the first and second electrodes for delivery of the medicament.

Figure 2:
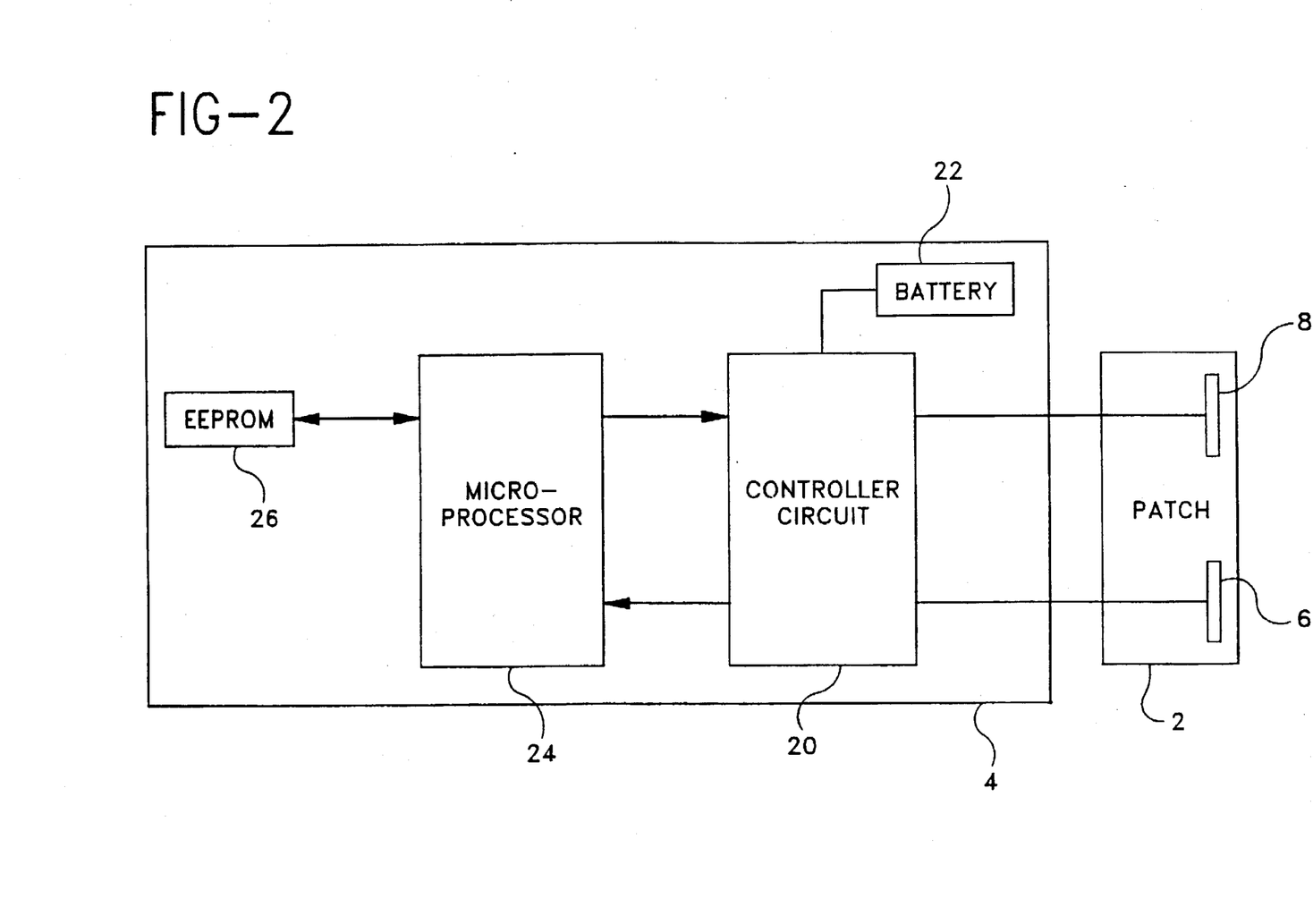
FIG. 2 is a functional block diagram of the iontophoretic drug delivery system formed in accordance with the present invention.

Referring now to FIG. 2, one form of the iontophoretic drug delivery device having an improved controller 4 is shown coupled to patch 2. In a preferred embodiment, the controller 4 includes controller circuit 20, microprocessor 24 and E²PROM 26 electrically coupled thereto. The microprocessor preferably coordinates all controller functions. Among their other functions, the E²PROM, microprocessor, and controller circuit, together serve to monitor the current provided to, and the voltage across, the electrodes of the patch to ensure proper delivery of a medicament. A suitable microprocessor is part no. PIC 16C71-04/50 manufactured by Microchip Technology Inc. of Chandler, Ariz. As will be explained in more detail below, using known electronics and the E²PROM, microprocessor and controller circuit, a variety of additional iontophoretic drug delivery functions are monitored within the controller to provide proper safe drug delivery. The functions provided by the controller circuit include safety, current control and delivery, system control, and user interface functions.

Figure 3:
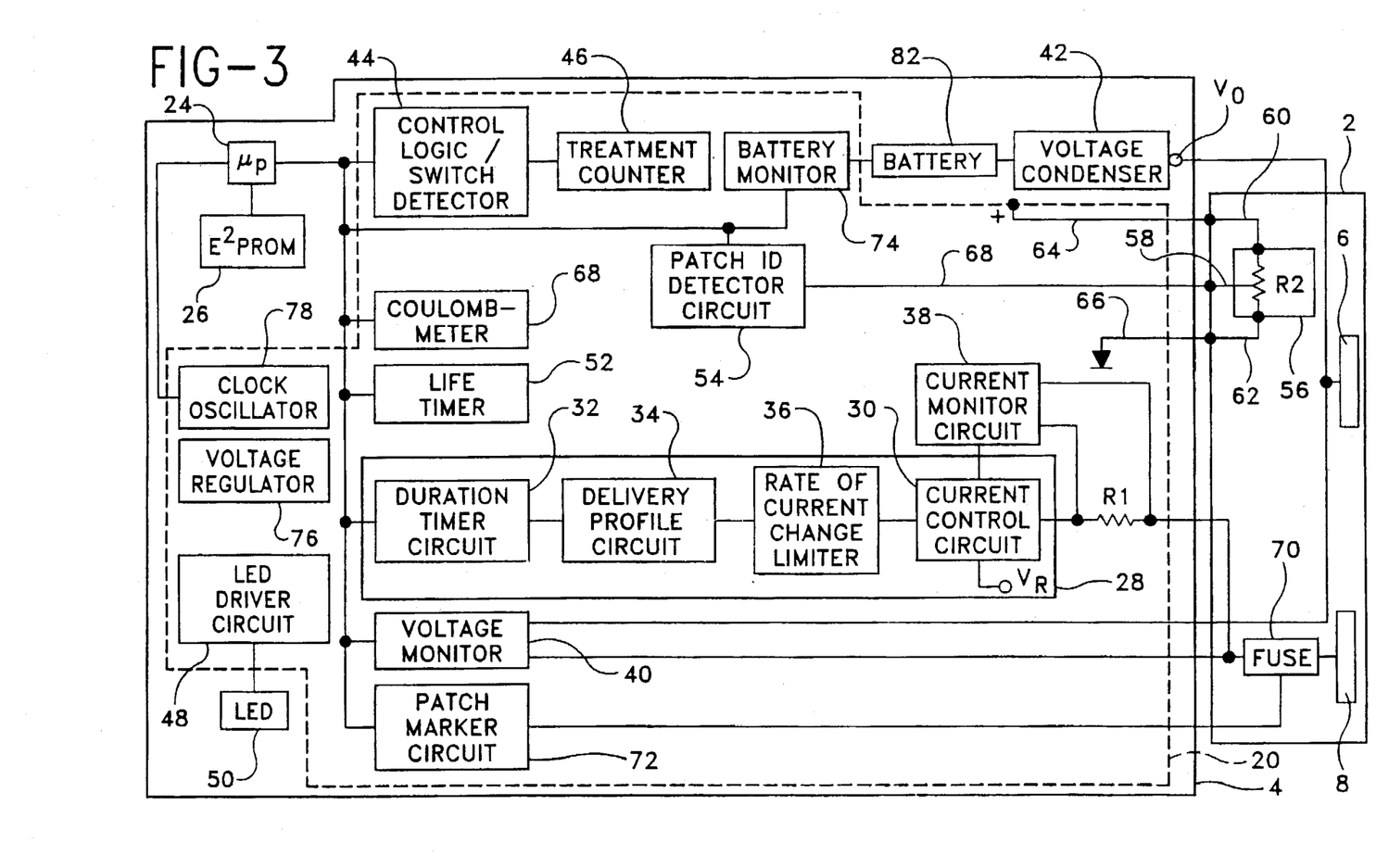
FIG. 3 is a detailed schematic diagram of the iontophoretic drug delivery system shown in FIG. 2 formed in accordance with the present invention.

Referring now to FIG. 3, a more detailed form of the present invention will be described.

As shown in FIG. 3, the controller circuit 20 also includes an adjustable current regulator circuit 28 coupled to the microprocessor 24. The adjustable current regulator circuit preferably includes a current control circuit 30, which is coupled to the second electrode 8 (i.e., cathode) of the transdermal patch 2. As is known in the art, the current control circuit 30 is adjustable to generate a desired current flow through the first and second electrodes 8, 10 and the epidermis 10 of the patient undergoing iontophoresis. The current control circuit may be a series pass regulator, for example, and may be controlled by a voltage $V_r$ on an input of the circuit. By adjusting voltage $V_r$, the current control circuit 30 may function as a source or sink of a desired drug delivery current flowing through the patch electrodes 6, 8 and epidermis 10 of the patient. The current control circuit is advantageously designed with the capability of providing an adjustable but regulated current through the electrodes for proper drug delivery. The current control circuit, as is known in the art, has the ability to react to sudden changes in voltage and current requirements due, for example, to changes in the patient's skin impedance or changes in the impedance of the patch 2.

In a preferred form of the invention, the current regulator circuit 28 also includes a duration timer circuit 32, a delivery profile circuit 34, and a rate of current change limiter circuit 36 operatively coupled to the current control circuit 30. The duration time circuit 28, rate of current change limiter circuit 36 and current control circuit may have fixed parameters set at the time of manufacture, or have parameters that are controlled and changed by the microprocessor. Alternatively, the delivery profile circuit 34 is part of the microprocessor and stores the delivery instructions for a variety of drugs. In operation, the current regulator circuit 28 receives an electronic signal from the microprocessor 24 advising the current regulator circuit to commence drug delivery (i.e., generate a current flow to the patch electrodes). Depending upon the specific drug to be delivered by the patch, a patch identification signal is provided to the microprocessor by a patch ID detector circuit 54. The microprocessor, in response, generates a control signal specifying the characteristics of the delivery current consistent with the drug contained in the patch (i.e., duration, rate of current delivery, etc.). Each component of the current regulator circuit (i.e., the duration timer circuit 32, delivery profile circuit 34, rate of current change limiter circuit 36 and current control circuit 30) will coordinate their respective functions in accordance with the specific drug being delivered as identified by the patch identification signal.

Referring again to FIG. 3, the adjustable current regulator circuit 28 preferably includes a duration timer circuit 32 operatively coupled to the current delivery circuit 30 and the microprocessor 24. The duration timer circuit 28, utilizing circuitry as is known in the art, controls the duration of current delivery provided to the patch. In one embodiment, the duration timer circuit receives an electronic signal from the microprocessor indicating that delivery will begin. The duration timer circuit, which preferably includes a clock, will then note the start of current delivery to the patch and provide a signal, either to the microprocessor or current control circuit, effectively terminating current delivery after the specified time has elapsed. Preferably, the duration timer circuit is capable of varying the delivery time in accordance with the particular drug being delivered and the prescribed manner of delivery.

The adjustable current delivery circuit 28 also preferably includes a delivery profile circuit 34 operatively coupled to the current control circuit 30 and the microprocessor 24. In a preferred form of the invention, the delivery profile circuit includes sufficient memory to store specific drug delivery procedures for a variety of drug applications (i.e. prescriptions). The delivery profile circuit preferably receives an electronic signal from the microprocessor identifying the specific drug to be delivered as provided by the patch ID detector circuit 54 and/or an identification of the amount and duration of current to be applied to the patch 2. In response, the delivery profile circuit 34, which includes known circuitry including memory, accesses the proper drug application prescription corresponding to the patch, and provides a current profile signal to the current control circuit 30 describing characteristics of current delivery that is to occur. Specifically, the profile signal describes the magnitude of the current flow and whether the current applied to the patch is to have a substantially constant value, or whether the current flow waveform is to take the form of a square wave, saw-toothed wave, pulse-train, sinusoid or any other desired waveform. In response to the profile signal, the current control circuit 30 will provide a current flow to the cathode of the patch in accordance with the profile signal.

The adjustable current regulator circuit 28 also preferably includes a rate of current change limiter circuit 36 operatively coupled to the current control circuit 30 and the microprocessor 24. Using known circuitry, the rate of current change limiter circuit 36 preferably monitors the current flow being delivered by the current control circuit 30 to the patch and prevents the current control circuit from changing to a new rate of current delivery faster than a predetermined rate of change in order to prevent patient discomfort which could result from too fast a change in the rate of current flow.

The adjustable current regulator circuit 28 shown in FIG. 3 operates in the following manner. A voltage $V_r$ is preferably controlled by the delivery profile circuit 34 and applied to the current control circuit 30 which will cause a corresponding desired current flow. The current flow will traverse through one of the electrodes 6, 8 of the transdermal patch 2 and through the patient's skin 10 when the patch is placed on the patient. The patient and patch together will have a particular impedance Z, which, as is known, may vary.

For example, if the impedance of the patch and patient together is 15,000 ohms, and the desired drug delivery current flowing through the patch and patient is set for 2 milliamperes by the delivery profile circuit 34, then by Ohm's law, there will be a voltage drop across the patch/patient of 30 volts. These would be, as an example, the expected impedance and desired drug delivery current flow for a particular medication being applied transdermally.

However, it is known that the impedance of a patient's skin can range from over 100,000 ohms to less than 1,000 ohms, depending on the duration that the iontophoretic current is applied, the magnitude of the current which is being delivered, the location of the system on the patient's body, and a variety of other known factors. In a system where the desired current level, which is determined in part by the drug administered to the patient, is for example 2 milliamperes, a voltage potential of 100 volts would result if the skin impedance is 50,000 ohms. Such a voltage would cause undesirable sensations to the user and may result in skin irritation or burns. Therefore, it is foreseen that the present invention includes an adjustable current regulator circuit to ensure that this will not occur and at the same time providing the minimum voltage and current flow necessary for drug delivery.

The controller circuit 20 of the present invention also preferably includes a current monitor circuit 38 operatively coupled to the current control circuit 30 and the microprocessor 24. The current monitor circuit, utilizing circuitry known in the art, determines the magnitude of current flow provided by the current control circuit. If the current flow is greater than a first predetermined value or less than a second predetermined value, a corresponding electronic signal is provided to the microprocessor which in turn provides a control signal to the current control circuit and/or a voltage converter to modify the amount of current being delivered to the patch to ensure efficient and safe iontophoretic drug delivery. In one embodiment, the current monitor circuit 38 substantially comprises a resistor $R_1$ of known value, in series with the current control circuit and the second electrode 8. The current monitor circuit also preferably includes a comparator or operational amplifier having its non-inverting input coupled to one input of the resistor $R_1$ and its inverting input coupled to the other input of the resistor $R_1$. Based on the voltage drop detected, the amount of current provided by the current regulator circuit can be readily determined and modified as the impedance characteristics of the patch and patient change.

In a preferred embodiment, the current monitor circuit 38 is an independent control loop which, when presented with a desired current rate, will maintain the desired current rate utilizing feedback from a voltage measured across a small sampling resistor $R_1$ through which the current passes. The microprocessor monitors the value of the current flow detected by the current monitor circuit to confirm that the current flow is substantially equal to the desired current flow. As a result, current monitor circuit serves as an independent monitor of the actual current flow.

As is shown in FIG. 3, the controller circuit 20 of the present invention also preferably includes a voltage monitor circuit 40 operatively coupled to both the first and second electrodes 6, 8 of the patch 2 and the microprocessor 24. The voltage monitor circuit 40, utilizing circuitry known in the art such as an operational amplifier or comparator, continuously determines the voltage drop across the first and second electrodes and provides the voltage information to the microprocessor 24. If the voltage detected across the first and second electrodes is greater than a first preselected value or less than a second preselected value, the microprocessor will provide a control signal to the current control circuit 30 and/or a voltage converter to modify the voltage drop across the patch electrodes to ensure efficient and safe iontophoretic drug delivery. If the voltage detected across the first and second electrodes by the voltage monitor exceeds a predetermined safe limit, the voltage monitor will cause the controller to cease current delivery.

In some applications, it may desirable to increase the voltage provided to the patch electrodes from that provided by the power source. This is especially true when the iontophoretic device is battery powered, and it may be necessary to increase a relatively low battery voltage to a higher, but safe, electrode voltage to more effectively drive the ionic medication into the skin and tissue of the patient.

Referring again to FIG. 3 and in a preferred form of the present invention, the controller includes a voltage converter 42 electrically coupled to the battery 22. The voltage converter, using circuitry, for example as described in the present inventor's co-pending patent application entitled "Iontophoretic Drug Delivery Device Having High-Efficiency DC-to-DC Conversion Circuit" filed Aug. 29, 1995, U.S. application Ser. No. 08/520,521, pending the disclosure of which is incorporated herein by reference in its entirety, is also electrically coupled to the first electrode 6 (anode) and to the second electrode 8 (cathode) of the patch 2. The voltage monitor 40 is preferably electrically coupled to both the first and second electrodes of the patch 2. As previously explained, the voltage monitor 40 detects the absolute difference in voltage between the first and second electrodes. Preferably, the voltage converter 42 adjusts its output voltage in response to the detected voltage drop to provide a voltage converter output voltage ($V_o$) between ground and at least one of the electrodes. The voltage converter output voltage ($V_o$) corresponds to the voltage across the electrodes which provides safe and effective drug delivery to the patient without the wasteful consumption of power. The voltage converter may be a step-up converter which effectively increase the battery voltage. Such a step-up converter would be useful in a wearable portable iontophoresis system which is battery powered.

Alternatively, it is envisioned that the voltage converter 42 may provide an output voltage which is equal to the power source (battery) voltage, in order to isolate the patient directly from the battery. The voltage converter 42 may even be a step-down converter, providing an output voltage which is less than the voltage of the battery. In any event, it is preferred if the voltage converter is adjustable so that it may vary the output voltage in response to a control signal (such as a feed back voltage level) provided to it by the voltage monitor and/or microprocessor.

In one embodiment of the present invention, the controller includes a controller circuit 20 including a control logic/switch detector 44 and treatment counter 46 electrically coupled to the microprocessor 24 and current control circuit. One system for counting the number of drug applications performed by the controller is disclosed in my co-pending U.S. patent application Ser. No. 08/315,377 filed Sep. 30, 1995, now abandoned, the disclosure of which is incorporated herein by reference in its entirety. The control logic/switch detector 44 serves in one function, as an interface with the microprocessor and interprets the control delivery sequence to the microprocessor. The control logic/switch detector also interprets user activated controls to turn the system on or off. In a preferred embodiment, the control logic/switch detector includes among other elements, suitable electronics to detect the activation of an external single pole-single throw (SPST) switch. Once the activation of the SPST switch is detected by switch detector, the control logic/switch detector instructs the microprocessor as to when the user is ready to begin operation and initializes the electronic circuit 20 for drug delivery. In an alternative embodiment, the control logic and switch detector functions are individual functions requiring separate electronic circuits.

Electrically coupled to the control logic/switch detector 44 is a treatment counter 46. The treatment counter senses each time the switch of the control logic/switch detector is activated (i.e., each time the microprocessor begins drug delivery) and maintains a running total of the number of times the switch detector has been activated. Preferably, once the treatment counter 46 determines that a specified number of applications have occurred, for example 200, the treatment counter provides an electronic control signal via the control logic/switch detector to the current regulator circuit 30 and/or microprocessor 24 effectively stopping the current flow and corresponding drug delivery. As a result, the controller 4 is effectively disabled and is prevented from providing further applications of current to a patch to which the controller may be coupled now or in the future. In this way, it can be assured that the battery 22 within the controller has sufficient energy to properly deliver the medicament from the patch to the patient's body in accordance with the prescribed duration and profile. The controller circuit may also preferably include means to indicate that the useful life of the controller has been exhausted. For example, the controller 4 may also include a visual (or audible) indicator. In this embodiment, a light emitting diode (LED) or liquid crystal display (LCD) driver circuit 48 as known in the art can be coupled to the microprocessor 24. The LED driver circuit 48 preferably has an LED 50 coupled thereto which will be activated or deactivated when the specified number of medicament applications have occurred.

Another purpose for the inclusion of a treatment (usage) counter involves prescriptions that specify a particular number of drug applications. In this embodiment, the treatment counter is programmed by the pharmacist or doctor prior to delivery to the patient so that only a specific number of applications of medicament may occur. Furthermore, the treatment counter can maintain a record of the achieved number of times the device has been used. The device can then be presented as proof of use to the physician or insurance company for reimbursement purposes.

In an alternate embodiment and as shown in FIG. 3, the controller 4 may also include a device life timer 52 operatively coupled to the microprocessor. The device life timer preferably includes a clock and is designed to store the useful life time limit of the controller. For example, it may be determined that the controller battery and electronics have a specific life expectancy, based upon the preprogrammed power requirements and shelf life, to provide iontophoretic drug deliveries for approximately five years. The clock of the device life timer may be activated at the time of manufacture of the controller or at any other suitable time. When the device life timer determines that the preprogrammed amount of continuous time from manufacture has expired (i.e., five years), the device life time preferably provides an electronic control signal to the current regulator circuit 28 and/or microprocessor 24 effectively disabling the controller. At such time, the controller will be rendered unusable and may be discarded or returned to the manufacturer for refurbishment. The microprocessor may then send an electronic signal to the LED driver 48 to visually indicate to the user via LED 50 that the controller's predetermined useful life has expired and that the controller can no longer be used. The manufacturer can thus be assured that an out-of-date controller can be rendered unusable, and this safety technique may satisfy some of the product liability concerns of the manufacturer.

When using an iontophoretic drug delivery device having a reusable controller 4, it would also be advantageous to identify which patient has a particular controller. Such a design would be beneficial to recall or retrofit particular controllers. In this alternative embodiment, a unique serial number may be embedded in the controller during manufacture or at a specific time thereafter. Referring to FIG. 3, the controller 4 further includes a read only memory (ROM) coupled to the microprocessor 24 for storing the unique serial number. In the preferred embodiment, the ROM is an $E^2$PROM which may be programmed to permanently store the unique serial number. The unique serial number can be read through a serial communication port (not shown) by a health-care professional to determine the identification of the controller. The traceability of the reusable controller is significantly enhanced by the readable unique serial number. Accordingly, a doctor or outside agency will be able to check the controller serial number to ensure that the patient has received the correct controller and can advise the user of recall or retrofitting information.

The iontophoretic drug delivery device of the present invention may also be specifically designed to ensure compatibility of the controller with the patch to which it is connected. Since different medicaments require different amounts of current for delivery, patch-controller compatibility is an important feature in order to avoid supplying an incorrect amount of energy to the patch which could possibly harm the patient or deliver an unprescribed amount of medicament. The controller may also be specifically programmed to deliver either an anionic or cationic drug. Thus, compatibility of the controller to the patch is very important. Accordingly, in the present invention, the controller, patch or both includes means for determining whether the controller is compatible with the patch. If it is determined that the patch and controller are incompatible, power is prevented from being supplied to the patch. In an alternative embodiment, after the controller identifies that it is coupled to a particular patch, the microprocessor may select an appropriate current delivery profile from a selection table or may calculate the proper delivery rate or profile based upon the patch identification. One system for ensuring compatibility of the controller with the patch is disclosed in my co-pending U.S. application Ser. No. 08/315,372 filed Sep. 30, 1995, pending, the disclosure of which is incorporated herein by reference in its entirety.

Referring again to FIG. 3, the controller circuit 20 preferably includes a patch ID detector circuit 54 operatively coupled to the microprocessor 24. As shown in FIG. 3, when the controller 4 is operatively coupled to the patch 2, a patch ID indicator 56 located within patch 2 is electrically coupled to the controller and the patch ID detector 54. Preferably, the patch ID indicator 56 comprises a resistor $R_2$ which is formed from an elongated resistive material that is tapped by electrical lead 58 at a desired point along the resistors length. The resistor $R_2$ is coupled at one end to electrical lead 60 and at its other end to electrical lead 62. The patch ID detector circuit 54 of the controller includes electrical leads 64, 66 and 68. Preferably, when the controller is mated to the patch, electrical lead 64 of the controller is electrically coupled to electrical lead 60 of the patch, electrical lead 66 of the controller is electrically coupled to electrical lead 62 of the patch, and electrical lead 68 of the controller is electrically coupled to electrical lead 58 of the patch. In this embodiment, electrical leads 60 and 62 of the patch are coupled to a voltage source. When coupled to the voltage source, a unique voltage on electrical line 68 is provided depending upon the selected location of the tapped electrical lead 58 on resistor $R_2$.

The patch ID detector 54 of the controller preferably includes a comparator, as known in the art, to compare the voltage detected on electrical line 68 to a known voltage to determine whether the drug delivery patch 2 is compatible with the controller 4. If the voltage on electrical lead 68 corresponds to a known voltage stored in the patch ID detector, the patch and controller are deemed to be compatible. However, if the voltages do not coincide, the patch and controller are deemed incompatible. In the first situation, an electrical signal is provided by the patch ID detector 54 to the microprocessor 24 instructing the microprocessor to begin delivery when the control logic/switch detector 44 is activated. In the second situation, an electronic control signal is provided by the patch ID detector 54 to the microprocessor instructing the microprocessor that the patch is incompatible and that delivery of the medicament in the patch should not take place even if the control logic/switch detector is activated. In an alternative embodiment, the current passing through resistor $R_2$ that is induced by the voltage source is measured by the patch ID detector to determine a specific patch identification and its compatibility with the controller.

In yet another embodiment, the compatibility of the patch and controller may be determined by use of an electronic serial number stored in a ROM or integrated chip embedded in the patch wherein the patch ID detector 54 includes means for reading the serial number. As previously explained, the patch ID detector 54 is capable of being electrically coupled to the patch when the controller and patch are connected, so as to read the serial number. In this embodiment, the patch ID detector 54 is electrically coupled to the microprocessor 24 such that the patch ID detector may poll the patch to determine if the serial number is found in a look-up table stored in the $E^2PROM$ of the controller. If the serial number is not compatible with the particular controller, the controller will be prevented from supplying energy to the patch. However, if the serial number stored in the patch matches that stored by the patch ID detector 54, the microprocessor and control logic will be ready to coordinate delivery of the medicament.

In addition to the above, it would be advantageous for health-care professionals to have the ability to determine if the patient is receiving the desired dosage of medication during each delivery. Therefore, in one embodiment of the present invention shown in FIG. 3, the $E^2PROM$ 26 of the controller has a real-time clock (not shown) coupled thereto to provide the date and time information, and the $E^2PROM$ has sufficient memory available to be able to record the date, time and/or duration of drug delivery. The information may then be played back by a medical technician or health-care professional. This becomes extremely important in monitoring a patient who is iontophoretically administering a drug in an unsupervised setting. Using known electronics, the controller voltage, current, and duration of use can also be recorded and stored for subsequent retrieval. The stored information may be played back through a serial communications port (not shown) of the controller.

In an alternative embodiment, the controller includes a light emitting diode 50 (LED) which can transmit and receive information. The LED is electrically coupled to the microprocessor 24 so that information stored by the microprocessor can be transmitted via the LED to a technician or health-care professional. The stored data may be transmitted by the LED to a computer and displayed using any known display means. Additionally, when not transmitting, the LED can be used as a photo-receiver for providing instructions to the microprocessor 24. Accordingly, the improved iontophoretic drug delivery controller allows for two-way communication including transmission of data and reception of new drug delivery instructions without disassembly of the controller. The circuitry for performing the transmission and reception of data using LED's, such as an LED driver circuit 48, is well known to those skilled in the art and any such known transceiver circuitry may be used.

As previously identified, it would be helpful to know the total number of coulombs provided by the controller to the patch and the patient in order to ensure that the total number of electrons passed to the patient does not exceed the available number of drug molecules. Therefore, the controller preferably includes a coulombmeter 68 operatively coupled to the microprocessor 24. In a preferred form of the invention, the coulombmeter 68 includes an electronic circuit, as known in the art, for receiving information related to the rate of current delivery and the duration of current delivery. In response to this information, the coulombmeter effectively determines the total number of coulombs provided by the controller. This information may be stored in the coulombmeter itself or in the $E^2PROM$ 26 for retrieval by a health-care professional at a later time.

In order to ensure proper delivery of a drug, the iontophoretic drug delivery system of the present invention further includes means which disables the patch and/or controller circuit once the supply of medicament of the patch has been exhausted (i.e., when delivery is complete). In a preferred form of the invention, and as shown in FIG. 3, the patch 2 includes a fuse 70 or heat sensitive element coupled between the second electrode 8 (i.e., cathode) and the current control circuit 30. In addition, the controller circuit 20 includes a patch marker circuit 72 operatively coupled to the control logic and microprocessor 24. As shown in FIG. 3, when the controller 4 is coupled to the patch 2, the patch marker circuit 72 is electrically coupled to the fuse 70.

Once the microprocessor is advised that the supply of medicament on the patch has been exhausted, the microprocessor preferably advises the patch marker circuit 72 to provide sufficient energy to activate the fuse 70 opening the circuit to the second electrode effectively disabling the patch 2. In this way, the controller will not be able to deliver current to the electrodes of a patch that previously delivered substantially all of its medicament. As a result, the problems associated with applying current to the user without delivering a medicament can be avoided. The fuse 70 or heat sensitive element may be arranged such that a visible indication of a used patch is perceivable to the patient or medical personnel. The microprocessor 24 may also provide an electronic signal to the patch marker circuit 72 each time the controller is coupled to a patch to poll the fuse 70 to determine if the fuse has been activated. If the fuse is determined to be blown, the microprocessor 24 will prevent the controller circuit 20 from applying current to the patch.

In another embodiment of the present invention, the controller circuit 20 preferably includes a battery monitor circuit 74 operatively coupled to the battery 22 and the microprocessor. Using known electronics, the battery monitor circuit preferably monitors the energy remaining in the battery. The battery monitor may provide a direct indication of the amount of change remaining in the battery. Alternatively, the battery monitor circuit may provide a signal to the microprocessor 24 which will activate LED 50 via LED driver circuit 48 to advise the user as to whether sufficient energy remains in the battery to ensure reliable drug delivery.

The controller circuit 20 also includes a voltage regulator 76 and a clock oscillator 78. The voltage regulator is operatively coupled (not shown) to each of the circuits of the controller circuit in order to assure that each of the circuits is biased at an appropriate voltage independent of the battery voltage. The clock oscillator 78 is operatively coupled to the microprocessor 24 to provide the clock input synchronization signal for operation of the microprocessor.

In a preferred form of the present invention, the controller circuit 20 including each of its corresponding functions, features and circuits, is embodied in an application specific integrated circuit (ASIC). The ASIC preferably includes the integration of substantially all of the active electronic components of the controller, independent of their operating voltage. The ASIC is designed to include functions performed by individual circuits in traditional controllers. Specifically, the ASIC includes incorporation of the current control circuit 30, the current delivery duration timer circuit 32, the current delivery profile circuit 34, the coulometer 68, the rate of current change circuit 36, the voltage monitor circuit 40, the current monitor circuit 38, light emitting diode driver circuit 48, a control logic/switch detector 44, clock oscillator 88, device life timer circuit 52, treatment counter circuit 46, battery monitor 75, real-time clock, and an iontophoretic drug delivery patch detector circuit 54. Alternatively, the microprocessor could also be embodied in the ASIC with the other controller functions.

By fabricating the circuitry of each of the iontophoretic functions on the ASIC, a significantly smaller controller can be provided than was realized in prior art iontophoretic systems. Additionally, since all active components will be incorporated in the ASIC, and the ASIC is fabricated under stringent guidelines (i.e., clean rooms) the reliability of the controller will not be dependent on the reliability of numerous individual discrete components. Instead, the reliability of the controller will be increased because the reliability will be related to the failure rate of the ASIC, not a plurality of individual components that have to be hand-wired and soldered together. In addition, since the components integrated in the ASIC require less power then traditional discrete components, power consumption of the present system embodied in an ASIC is reduced over that of the prior art which permits the integration of a smaller power source in the controller thus reducing the cost over that of traditional controllers.

As can be seen from the above description, the present invention offers many features that are needed in the administration of a variety of medicaments by the use of iontophoretic devices. The improved controller of the present invention is capable of delivering a variety of medicaments in a variety of manners, and of maintaining and recording important information for play-back to health-care professionals. Additionally, the controller and patch design includes important safety features to ensure the patient's safety against the misapplication of medicaments and the application of excessive current. The present invention is designed to be more compact and reliable than known systems.

Although illustrative embodiments of the present invention have been described herein with reference to accompanying drawings, it is to be understood that the invention is not limited to those precise embodiments, and that various other changes and modifications may be effected therein by one skilled in the art without departing from the scope or spirit of the invention.

what is claimed:

1. An iontophoretic drug delivery system comprising:
    a medicament containing patch removably attachable to the skin of a user for transdermal delivery of a medicament, the patch having at least a first electrode and a second electrode, the medicament including a plurality of drug molecules;
    a reusable controller removably electrically coupled to the patch, the controller providing sufficient energy to the patch to deliver the medicament from the patch into the skin of a patient; and
    a current delivery safety circuit operatively coupled to the controller for assuring the substantially safe delivery of the medicament from the patch into the skin of the patient, the current delivery safety circuit including:
    a coulombmeter electrically coupled to at least one of the first electrodes and second electrodes for monitoring a total number of electrons delivered through the patch, the coulombmeter providing an output signal if the total number of electrons is at most substantially equal to the plurality of drug molecules;
    a current monitor circuit operatively coupled to at least one of the first electrode and second electrode for monitoring a rate of current flow through the patch, the current monitor circuit providing an output signal if the rate of current flow is at least equal to a first preselected value and at most equal to a second preselected value;
    a patch identification detector electrically coupled to the patch, the patch identification detector providing an indication as to whether the patch and the controller are deemed incompatible, patch identification detector preventing a supply of energy to the patch sufficient to deliver the medicament from the patch into the skin of the patient if the patch and controller are deemed incompatible;

a patch marker circuit electrically coupled to at least one of the first electrode and second electrode of the patch, the patch marker circuit substantially permanently disabling the patch when substantially all of the medicament has been delivered from the patch to the skin of the patient; and a voltage monitor circuit operatively coupled to the first electrode and the second electrode for monitoring a voltage therebetween, the voltage monitor providing an indication if the voltage potential between the first and second electrodes is at least greater than a first predetermined value and at most equal to a second predetermined value.

2. An iontophoretic drug delivery system comprising:

a medicament containing patch removably attachable to the skin of a user for transdermal delivery of a medicament, the patch having at least a first electrode and a second electrode;

a reusable controller removably electrically coupled to the patch, the controller including an energy source for providing sufficient energy to the patch to drive the medicament from the patch into the skin of the patient; and a user interface circuit for at least one of providing and receiving information to the user, the user interface circuit including:

a battery monitor circuit electrically coupled to the energy source for monitoring an amount of energy stored in the energy source and providing a battery monitor signal in response thereto;

a treatment counter circuit for counting the number of times the controller is used and providing a treatment counter signal in response thereto;

a device life timer circuit for determining when a predetermined time period has elapsed, the predetermined time period corresponding to the useful life of the controller, the device life timer generating a device life timer signal in response thereto;

a data storage device being responsive to and storing at least one of the battery monitor signal, the treatment counter signal and the device life timer signal, the data storage device providing a data storage signal in response to the at least one of the battery monitor signal, treatment counter signal and device life timer signal, and an LED driver circuit including an LED, the LED driver circuit being responsive to and providing a visual indication to a user of at least one of the battery monitor signal, the treatment counter signal, the device life timer signal and the data storage signal.

3. An iontophoretic drug delivery system comprising:

a medicament containing patch removably attachable to the skin of a user for transdermal delivery of a medicament; and a reusable controller removably electrically coupled to the patch, the controller providing sufficient current to the patch to drive the medicament from the patch into the skin of the patient, the controller further including a coulombmeter electrically coupled to the patch for detecting a total amount of current delivered from controller to the patch.

4. An iontophoretic drug delivery system as defined by claim 3, wherein the coulombmeter generates an output signal when the total amount of current substantially corresponds to the medicament in the patch being exhausted.

5. An iontophoretic drug delivery system as defined by claim 4, wherein the patch further includes a patch marker, the patch marker having a first condition indicative of medicament being present in the patch and a second condition indicative of medicament being substantially exhausted from the patch, and wherein the controller further includes a patch marker circuit operatively coupled to the patch marker, the patch marker circuit being responsive to the coulombmeter output signal and generating a signal which substantially permanently alters the patch marker from the first condition to the second condition.

6. An iontophoretic drug delivery system for delivering medication to an applied area of a user comprising:

an iontophoretic drug delivery patch for placement against the skin of the user, the iontophoretic drug delivery patch including at least first and second electrodes and a medicament; and a reusable controller including an electronic control circuit for regulating the delivery of the medicament to the skin of the user, the electronic control circuit providing sufficient current to the patch to drive the medicament from the patch into the skin of the user, the electronic control circuit being an application specific integrated circuit (ASIC), the electronic control circuit including a current control circuit operatively coupled to at least one of the first and second electrodes for providing a desired current flow through the at least first and second electrodes to deliver the medicament to the skin of the user, the electronic control circuit further including a coulombmeter operatively coupled to the current control circuit for measuring a total quantity of current flow provided to the at least first and second electrodes.

7. An iontophoretic drug delivery system as defined by claim 6 wherein the electronic control circuit includes a current monitor circuit operatively coupled to the at least first and second electrodes the current monitor circuit monitoring the current flow through the at least first and second electrodes.

8. An iontophoretic drug delivery system as defined by claim 6 wherein the electronic control circuit includes a voltage monitor circuit electrically coupled to the iontophoretic drug delivery patch for monitoring a voltage potential between the at least first and second electrodes.

9. An iontophoretic drug delivery system as defined by claim 6 wherein the iontophoretic drug delivery system includes at least one light emitting device (LED) and wherein the electronic control circuit includes a light emitting diode (LED) driver mechanism coupled to the at least one LED, the LED driver providing an LED control signal that alternately activates and deactivates the at least one LED in accordance with an operating state of the iontophoretic drug delivery system.

10. An iontophoretic drug delivery system as defined by claim 6 wherein the electronic control circuit includes a switch closure detection circuit coupled to a switch for activating the iontophoretic drug delivery system, the switch closure detection circuit monitoring the on/off switch to provide an indication of the current state of the iontophoretic drug delivery system.

11. An iontophoretic drug delivery system as defined by claim 6 wherein the iontophoretic drug delivery system includes a data memory circuit coupled to the electronic control circuit, the data memory circuit recording characteristics of the delivery of medicament from the iontophoretic drug delivery patch to the skin of the patient.

12. An iontophoretic drug delivery system as defined by claim 6 wherein the electronic control circuit includes a treatment counter circuit, the treatment counter circuit recording the total number of medicament applications provided by the controller.

13. An iontophoretic drug delivery system as defined by claim 6 wherein the iontophoretic drug delivery patch includes a patch identification number indicative of the type of medicament being delivered, and wherein the electronic control circuit includes a patch identification circuit, the patch identification circuit storing a controller identification number, the patch identification circuit being responsive to the patch identification number, the patch identification circuit determining whether the patch identification number.

14. An iontophoretic drug delivery system for delivering medication to an applied area of a user comprising:

an iontophoretic drug delivery patch for placement against the skin of the user, the iontophoretic drug delivery patch including at least first and second electrodes and a medicament; and a reusable controller including an electronic control circuit for regulating the delivery of the medicament to the skin of the user, the electronic control circuit providing sufficient current to the patch to drive the medicament from the patch into the skin of the user, the electronic control circuit being an application specific integrated circuit (ASIC), the electronic control circuit including a rate of current change limiter circuit electrically coupled to the iontophoretic drug delivery patch for monitoring a rate of change in the current flow from the at least first electrode to the at least second electrode, the rate of current change limiter circuit preventing a change of current rate greater than a predetermined rate of change thereby preventing patient discomfort.

15. An iontophoretic drug delivery system for delivering medication to an applied area of a user comprising:

an iontophoretic drug delivery patch for placement against the skin of the user, the iontophoretic drug delivery patch including at least first and second electrodes and a medicament; and a reusable controller including an electronic control circuit for regulating the delivery of the medicament to the skin of the user, the electronic control circuit providing sufficient current to the patch to drive the medicament from the patch into the skin of the user, the electronic control circuit being an application specific integrated circuit (ASIC), the electronic control circuit including a life timer circuit having a clock mechanism, the life timer circuit providing an indication of a remaining amount of useful life of the controller, the life timer circuit preventing activation of the iontophoretic drug delivery system if at least a predetermined time period has elapsed.

16. An iontophoretic drug delivery system for delivering medication to an applied area of a user comprising:

an iontophoretic drug delivery patch for placement against the skin of the user, the iontophoretic drug delivery patch including at least first and second electrodes and medicament;

a reusable controller including an electronic circuit for regulating the delivery of the medicament to the skin of the user, the electronic control circuit providing sufficient current to the patch to drive the medicament from the patch to the skin of the user, the electronic control circuit including:

a data memory circuit for recording characteristics of the delivery of medicaments from the iontophoretic drug delivery patch to the skin of the patient; and a light emitting diode (LED) driver circuit, the LED driver circuit providing a data signal indicative of the contents of the data memory circuit; and an LED, the LED being operatively coupled to the LED driver circuit for optically transmitting the contents of the data memory circuit a remote data recieving station for receiving optical transmissions from the LED.

17. An iontophoretic drug delivery system for delivering medication to an applied area of a user comprising:

an iontophoretic drug delivery patch, the patch including at least first and second electrodes, a medicament, and a patch marker, the patch marker having a first condition indicative of the medicament being present in the patch and a second condition indicative of the medicament in the patch being at least partially delivered; and a reusable controller including an electronic control circuit for regulating the delivery of the medicament to the skin of the user, the electronic control circuit providing sufficient current to the patch to drive the medicament from the patch into the skin of the user, the electronic control circuit including a patch marker circuit operatively coupled to the patch marker, the patch marker circuit generating a signal which substantially permanently alters the patch marker from the first condition to the second condition when the medicament in the patch is at least partially delivered.

18. An iontophoretic drug delivery system for delivering medication to an applied area of a user comprising:

an iontophoretic drug delivery patch for placement against the skin of the user, the iontophoretic drug delivery patch including at least first and second electrodes and a medicament; and a reusable controller including an electronic control circuit for regulating the delivery of the medicament to the skin of the user, the electronic control circuit providing sufficient current to the patch to drive the medicament from the patch into the skin of the user, the electronic control circuit including a rate of current change limiter circuit electrically coupled to the iontophoretic drug delivery patch, the rate of current change limiter circuit monitoring a rate of change in the current flow from the at least first electrode to the at least second electrode and preventing a change of current rate greater than a predetermined rate of change.

19. An iontophoretic drug delivery system for delivering medication to an applied area of a user comprising:

an iontophoretic drug delivery patch for placement against the skin of the user, the iontophoretic drug delivery patch including at least first and second electrodes and a medicament; and a reusable controller including an electronic control circuit for regulating the delivery of the medicament to the skin of the user, the electronic control circuit providing sufficient current to the patch to drive the medicament from the patch into the skin of the user, the electronic control circuit including a life timer circuit, the life timer circuit providing an indication of a remaining amount of useful life of the controller, the life timer circuit preventing activation of the iontophoretic drug delivery system if at least a predetermined time period has elapsed.

20. A disposable iontophoretic drug delivery patch for delivering medicament to an applied area of a user when the patch is mated to a reusable iontophoretic controller, the patch comprising:

at least one medicament for delivery to a user;

at least first and second electrodes, at least one of the first and second electrodes being in electrical communication with the at least one medicament;

means for electrically connecting the at least first and second electrodes to the iontophoretic controller;

a patch marker, the patch marker having a first condition indicative of full medicament being present in the patch and a second condition indicative of the medicament in the patch being at least partially delivered to a user, the patch marker permanently changing from the first condition to the second condition in response to a signal received from the iontophoretic controller wherein the first and second conditions are electrically detectable by the controller;

means for electrically interfacing the patch marker to the iontophoretic controller.

21. An iontophoretic patch, as defined by claim 20, wherein the patch marker includes an electrical fuse having a first terminal and a second terminal, the first condition being defined as electrical continuity between the first and second terminals, the second condition being defined as a substantially open circuit between the first and second terminals.

* * * * *